United States Patent
Gonnering

(10) Patent No.: US 6,835,082 B2
(45) Date of Patent: Dec. 28, 2004

(54) MONOPOLAR ELECTROSURGICAL MULTI-PLUG CONNECTOR DEVICE AND METHOD WHICH ACCEPTS MULTIPLE DIFFERENT CONNECTOR PLUGS

(75) Inventor: Wayne J. Gonnering, Littleton, CO (US)

(73) Assignee: ConMed Corporation, Utica, NY (US)

( * ) Notice: Subject to any disclaimer, the term of this patent is extended or adjusted under 35 U.S.C. 154(b) by 0 days.

(21) Appl. No.: 10/298,352

(22) Filed: Nov. 18, 2002

(65) Prior Publication Data

US 2004/0097117 A1 May 20, 2004

(51) Int. Cl.⁷ .............................................. H01R 27/00
(52) U.S. Cl. ...................................... 439/218; 439/909
(58) Field of Search ............................... 439/218, 223, 439/217, 909

(56) References Cited

U.S. PATENT DOCUMENTS

| | | | |
|---|---|---|---|
| 4,141,616 A | | 2/1979 | Gottlieb |
| 4,545,375 A | | 10/1985 | Cline |
| 4,708,661 A | * | 11/1987 | Morland et al. ............... 439/77 |
| 4,885,482 A | * | 12/1989 | Sharp et al. .................. 326/47 |
| 5,518,418 A | * | 5/1996 | Larabell ..................... 439/505 |
| 5,573,424 A | | 11/1996 | Poppe |
| 5,633,578 A | | 5/1997 | Eggers et al. |
| 6,068,627 A | | 5/2000 | Orszulak et al. |
| 6,126,465 A | | 10/2000 | Franks, Jr. |
| 6,203,344 B1 | * | 3/2001 | Ito ............................. 439/218 |

FOREIGN PATENT DOCUMENTS

EP        0947167        10/1999

* cited by examiner

Primary Examiner—Gary V. Paumen
Assistant Examiner—James R Harvey
(74) Attorney, Agent, or Firm—John R. Ley

(57) ABSTRACT

Each of a banana pin connector plug, a rolled sheet metal connector plug and a Bovie connector plug are electrically and mechanically connected an electrosurgical generator with a single adapter-less multi-plug connector device. These three connector plugs are prevalently used to connect foot-switched monopolar electrosurgical handpieces to the generator. A socket is moved into a position to connect to the banana pin connector plug, and the socket is moved out of position to permit a contact arm to move into contact with the rolled sheet metal connector plug and the Bovie connector plug.

40 Claims, 7 Drawing Sheets

MONOPOLAR ELECTROSURGICAL MULTI-PLUG CONNECTOR DEVICE AND METHOD WHICH ACCEPTS MULTIPLE DIFFERENT CONNECTOR PLUGS

CROSS REFERENCE TO RELATED APPLICATION

This invention is related to an invention for an Electrosurgical Generator and Method with Removable Front Panel Having Replaceable Electrical Connection Sockets and Illuminated Receptacles, described in U.S. patent application Ser. No. 10/298,707, which is filed concurrently herewith and assigned to the assignee of the present invention. The subject matter of this concurrently filed application is incorporated herein by this reference.

FIELD OF THE INVENTION

This invention generally relates to electrosurgery, and more specifically, to a new and improved electrical connector device and method for foot-switched monopolar electrosurgical handpieces and instruments which is capable of accepting multiple different types of electrical connector plugs, thereby avoiding the necessity to use adapters to connect the different types of handpieces and instruments to the electrosurgical generator.

BACKGROUND OF THE INVENTION

Electrosurgery involves applying relatively high voltage, radio frequency (RF) electrical power to tissue of a patient undergoing surgery, for the purpose of cutting the tissue, coagulating or stopping blood or fluid flow from the tissue, or cutting or coagulating the tissue simultaneously. The high voltage, RF electrical power is created by an electrosurgical generator, and the electrical power from the generator is applied to the tissue from an instrument or handpiece manipulated by a surgeon during the surgical procedure.

In monopolar electrosurgery, the handpiece includes a single active electrode. The active electrode is applied to the tissue, and the electrical energy travels from the electrosurgical generator, through a conductor to the handpiece, from the active electrode of the handpiece into the tissue of the patient, where the cutting, coagulating or simultaneous cutting and coagulating effect is achieved at the interface of the active electrode with the tissue. The electrical current is distributed into the patient, collected from the patient by a return electrode connected to the patient at a location remote from the surgical site, and is returned to the electrosurgical generator by an electrical conductor connected to the return electrode.

The surgeon controls the delivery of power to the handpiece by depressing a finger switch on the handpiece, or by stepping on a foot switch which is associated with the particular handpiece. Depressing a finger switch or stepping on a foot switch delivers an activation signal to the electrosurgical generator. The electrosurgical generator responds to the activation signal by delivering the high voltage RF electrosurgical energy to an active electrode of the handpiece with which the activation signal is associated.

The type of monopolar handpiece which has a finger switch includes a multiple-prong electrical connector which is connected to an electrical receptacle in the front panel of the electrosurgical generator. Most, if not all, of the finger-switched monopolar handpieces use the same type of multiple-prong electrical connector. Consequently, any finger-switched monopolar handpiece can be used with any type of electrosurgical generator, because of the standardized use of the same type of multiple-prong electrical connection for finger-switched monopolar handpieces.

On the other hand, there is no standardized electrical connection for monopolar handpieces which require a foot switch for activation. All foot-switched monopolar handpieces use an electrical connector plug with a single prong which fits within a prong-receiving connection receptacle located on the front panel of the electrosurgical generator. However, there are at least three different types and sizes of single-prong electrical connector plugs used for foot-switched monopolar handpieces. The three most prevalently used single-prong electrical connector plugs for foot-switched monopolar handpieces are a 4-millimeter banana pin connector, a rolled sheet metal 0.125 AMP connector, or an electrosurgical Bovie #12 connector. Most electrosurgical generators provide only a single prong-receiving receptacle on the front panel of the generator. Consequently, only one of the foot-switched monopolar handpieces will directly connect to the electrosurgical generator.

Adapters are used to connect the other types of foot-switched monopolar handpieces to electrosurgical generators. The usual adapter includes a prong which is of the configuration to be received by the single-prong connection receptacle in the front panel of the electrosurgical generator. The adapter also includes a socket which is of the configuration which can accept the type of single-prong electrical connector attached to the foot-switched monopolar handpiece or instrument which the surgeon desires to use. The adapter is connected to the electrosurgical generator, and the desired foot-switched monopolar handpiece is connected to the adapter, thereby connecting the preferred handpiece to the electrosurgical generator.

While such adapters have worked satisfactorily, certain difficulties in using them have arisen. It is necessary not to misplace the adapters. Keeping track of the adapters requires accounting for additional pieces of equipment in the operating room, which increases the complexity of the already-complicated tasks required to set up all of the equipment for a typical surgical procedure. It is relatively easy to misplace an adapter, because the adapter is not permanently connected to the electrosurgical generator. Inexperienced operating room personnel or cleaning personal may unknowingly or accidentally discard an adapter along with a disposable foot-switched monopolar handpiece after completion of the procedure. Most foot-switched monopolar handpieces in use today are of the disposable variety, so the possibility of disposing of an adapter along with the used handpiece is always present. Other disadvantages associated with using adapters are also recognized.

SUMMARY OF THE INVENTION

The invention involves a single electrical multi-plug connector device which has the capability of directly accepting and mechanically and electrically connecting to the three prevalent and different types of single-prong electrical connection plugs used to connect foot-switched monopolar electrosurgical handpieces to the electrosurgical generator. As a consequence of the present invention, it is no longer necessary to use adapters to connect the different types of foot-switched monopolar electrosurgical handpieces to the electrosurgical generator, and it is no longer necessary for the surgical operating room personnel to keep track of different types of adapters.

In general terms, the invention involves a multi-plug connector and a method for mechanically and electrically connecting each one of a banana pin connector plug, a rolled sheet metal connector plug and a Bovie connector plug to an electrosurgical generator. A passageway is defined through which the connection plugs are inserted for connection and withdrawn for disconnection. A socket connector is moved into and out of alignment with the passageway. The socket connector defines a socket into which the banana pin connector plug is inserted when the socket connector is moved into the passageway. A contact arm also moves into and out of alignment with the passageway. The contact arm moves into contact with the rolled sheet metal connector plug and the Bovie connector plug. Preferably, the socket is moved out of the passageway so that the rolled sheet metal connector plug can be inserted into the passageway. The movement of the socket and the contact arm are preferably interrelated so that the socket is moved into the passageway when the contact arm is out of the passageway, and vice versa. The socket and the contact arm are electrically connected to the electrosurgical generator.

A more complete appreciation of the invention and its scope, and the manner in which it achieves the above noted and other improvements, can be obtained by reference to the following detailed description of a presently preferred embodiment taken in connection with the accompanying drawings, which are briefly summarized below, and the appended claims.

DETAILED DESCRIPTION

Figure 1:
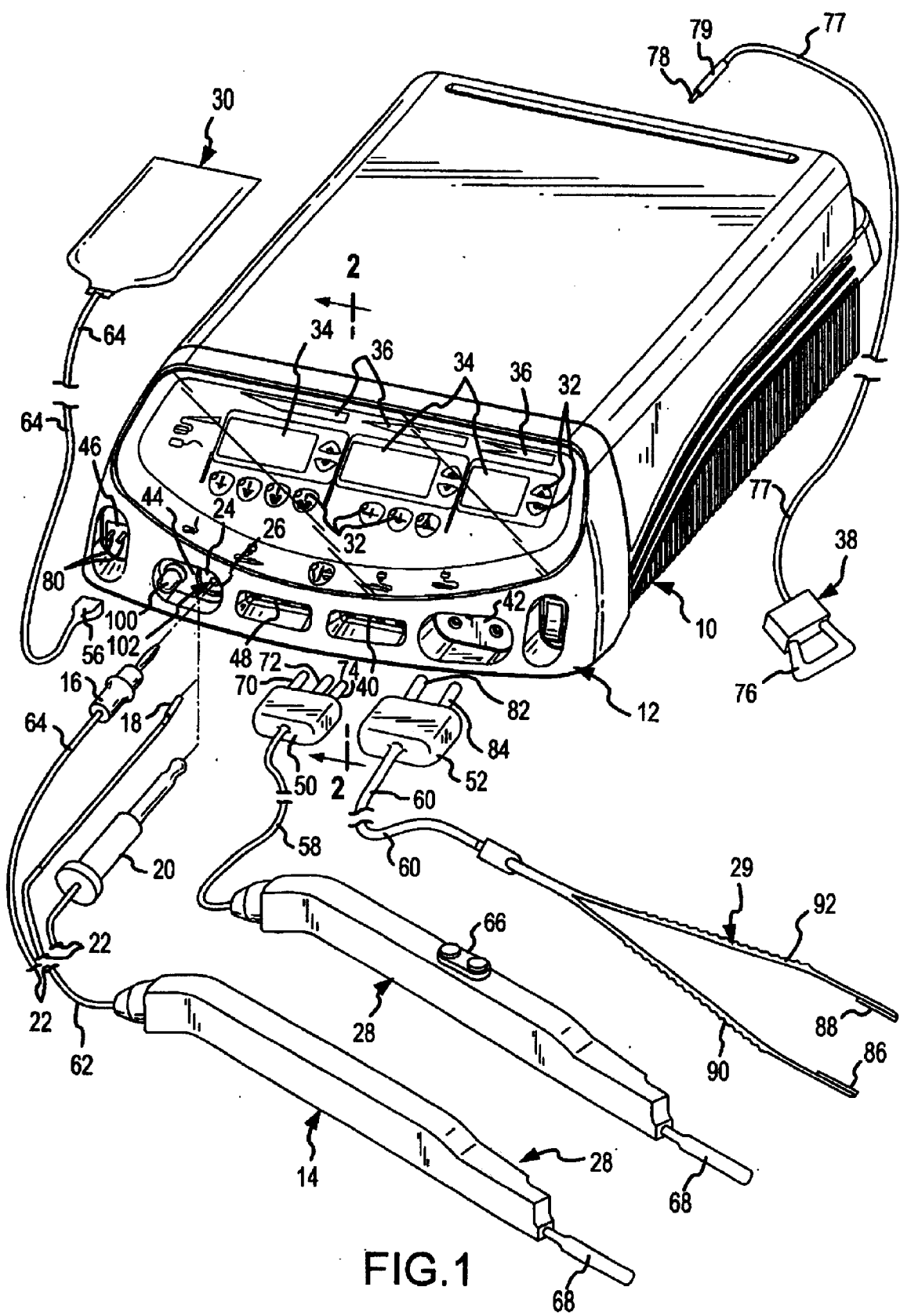
FIG. 1 is an external perspective view of an electrosurgical generator, and a typical foot-switched monopolar electrosurgical handpiece, a typical finger-switched monopolar electrosurgical handpiece, a typical bipolar electrosurgical handpiece, a typical foot switch, and a typical return electrode, all of which may be connected to the electrosurgical generator.

An electrosurgical generator 10, shown in FIG. 1, includes a front panel 12 at which to connect various conventional electrosurgical instruments and accessories, including a foot-switched monopolar handpiece 14. The foot-switched monopolar handpiece 14 is connected to any one of a conventional 4-millimeter banana pin connector plug 16, a conventional rolled sheet metal 0.125 AMP accessory connector plug 18, or a conventional electrosurgical Bovie #12 accessory connector plug 20. A conductor 22 extends from the foot-switched monopolar handpiece 14 to the one of the connector plugs 16, 18 or 20 which is connected to the handpiece 14. Because of the lack of standardization for connector plugs used with foot-switched monopolar handpieces in electrosurgery, any one of the connector plugs 16, 18 or 20 may be connected to the foot-switched monopolar handpiece 14. The present invention involves a multi-plug connector device 24, located within a receptacle 26 formed in the front panel 12, which is capable of directly mechanically accepting and directly electrically connecting any one of the different types of connector plugs 16, 18 or 20 without the need for an adapter.

In addition to the foot-switched monopolar handpiece 14, other handpieces and instruments which may be connected to the electrosurgical generator 10 include a finger-switched monopolar handpiece 28, a bipolar handpiece or forceps 29, and a return electrode 30. The front panel 12 also includes various touch input switch devices 32, displays 34 and indicators 36, which are used to control the operation of the electrosurgical generator by setting cut, coagulation or simultaneous cut and coagulation modes of electrosurgical operation and the amount of electrosurgical power to be delivered in the selected mode of operation, among other typical things. The front panel 12 functions as a user interface with regard to performing input/output tasks. A typical foot switch 38 is also connected to the electrosurgical generator 10, at a back or rear housing panel (not visible in FIG. 1). The foot switch 38 controls the delivery of power to the foot-switched monopolar handpiece 14 and to the bipolar forceps 29.

The front panel 12 locates and positions other electrical connector plug-receiving receptacles 40, 42 and 46 by which to electrically connect the finger-switched monopolar handpiece 28, the bipolar forceps 29, and the return electrode 30, respectively. The front panel 12 also includes another electrical connector plug-receiving receptacle 48 by which to connect an additional finger-switched monopolar handpiece (not shown) similar to the one shown at 28. The finger-switched monopolar handpiece 28, the bipolar forceps 29 and the return electrode 30 are each connected to an electrical connector plug 50, 52 and 56 which is inserted into the plug-receiving receptacles 40, 42 and 46 when connecting the finger-switched monopolar handpiece 28, the bipolar forceps 29 and the return electrode 30 to the electrosurgical generator 10, respectively. The connector plugs 50, 52 and 56 are electrically connected by conductors 58, 60 and 64 to the finger-switched monopolar handpiece 28, the bipolar forceps 29, and the return electrode 30, respectively.

The typical finger-switched monopolar handpiece 28 includes a finger activation switch 66 for the surgeon to depress to activate the electrosurgical generator 10 to deliver electrosurgical power from the plug-receiving receptacle 40 (or 48), to the connector plug 50, through the conductors 58 to the handpiece 28, and from an active electrode 68 connected at the distal end of the handpiece 28 to the tissue of the patient. One prong 70 of the connector plug 50 conducts the high voltage RF electrosurgical power through one of the conductors 58 to the active electrode 68. Two other prongs 72 and 74 of the connector plug 50 conduct activation signals from the activation switch 66 through the conductors 58 to the electrosurgical generator 10. The prong 72 conducts an activation signal from the finger switch 66 indicating that coagulation mode power is to be delivered to the active electrode 68, and the prong 74 conducts an activation signal from the finger switch 66 indicating that cut mode power is to be delivered to the active electrode 68.

The foot-switched monopolar handpiece 14 is similar to the finger-switched monopolar handpiece 28, except that the foot-switched monopolar handpiece 14 does not include a finger switch 66 to activate the electrosurgical generator 10. Instead, the foot-switched monopolar handpiece 14 requires the use of the foot switch 38 to activate the electrosurgical generator 10. The foot switch 38 includes a pedal 76 which is depressed by the foot of the surgeon, and in response, the foot switch 38 delivers an activation signal through conductors 77 to a prong 78 of a foot switch connector plug 79. The foot switch connector plug 79 is connected to the electrosurgical generator 10 in a receptacle located in the back housing panel (not shown in FIG. 1). In response to the activation signal from the foot switch 38, the electrosurgical generator 10 is activated and delivers electrosurgical power through the multi-plug connector device 24 to one of the connector plugs 16, 18 or 20 to which the foot-switched monopolar handpiece 14 is connected.

The electrical circuit for monopolar current flow is from the active electrode 68 through the patient to the return electrode 30. The return electrode 30 is attached to the skin of the patient at a location remote from the surgical site. The electrical current is collected from the patient's body by the return electrode 30, conducted through the conductors 64 and returned to the electrosurgical generator through connector plug 56 which is inserted into the plug-receiving receptacle 46. The plug receiving receptacle 46 for connecting the return electrode 30 includes a pair of male prongs 80 which extend into mating sockets (not shown) of the connector plug 56.

Electrical energy for bipolar electrosurgery performed with the bipolar forceps 29 is delivered from the plug-receiving receptacle 42 and conducted through prongs 82 and 84 of the connector plug 52. The electrosurgical energy is conducted from the plug-receiving receptacle 42 and into the prongs 82 and 84 of the connector plug 52, through the conductors 60 and delivered to electrodes 86 and 88 connected at the distal ends of arms 90 and 92 of the forceps 29. One of the electrodes 86 or 88 transfers current into the tissue confined between the two electrodes 86 and 88 by squeezing the arms 90 and 92, and the other electrode 86 or 88 collects and returns the current from the tissue. In bipolar electrosurgery, the electrosurgical current flows directly between the electrodes 86 and 88, making the use of the return electrode 30 unnecessary. The electrosurgical generator is activated to deliver the bipolar electrosurgical energy to the forceps 29 by depressing the pedal 76 of the foot switch 38, in the same manner as has been described for activating the foot-switched monopolar handpiece 14. Some types of bipolar forceps 29 include a switch which generates an activation signal upon squeezing the arms 90 and 92 together.

Figure 5:
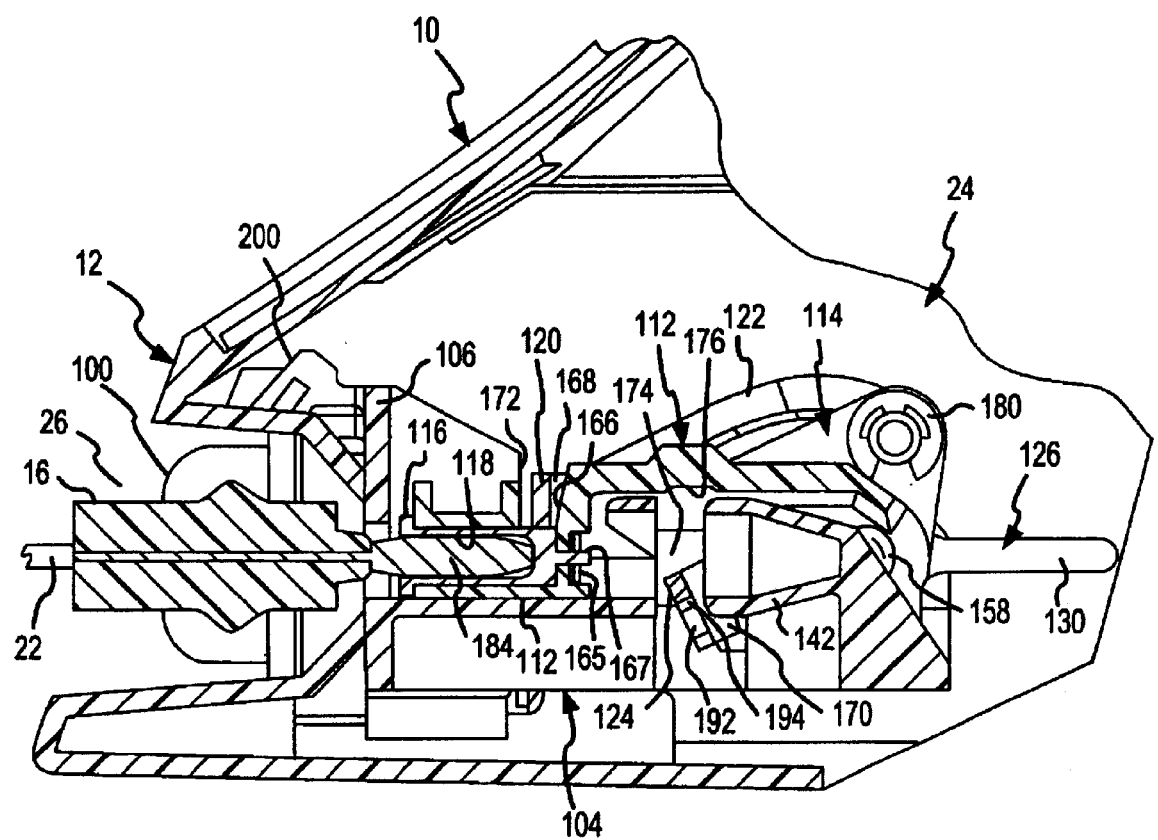
FIG. 5 is a side cross-sectional view of the multi-plug connector device shown in FIG. 4, taken substantially in the plane of line X—X in FIG. 4, and through a passageway in which a banana connector plug of the type shown in FIG. 1 is connected to the multi-plug connector device.
Figure 6:
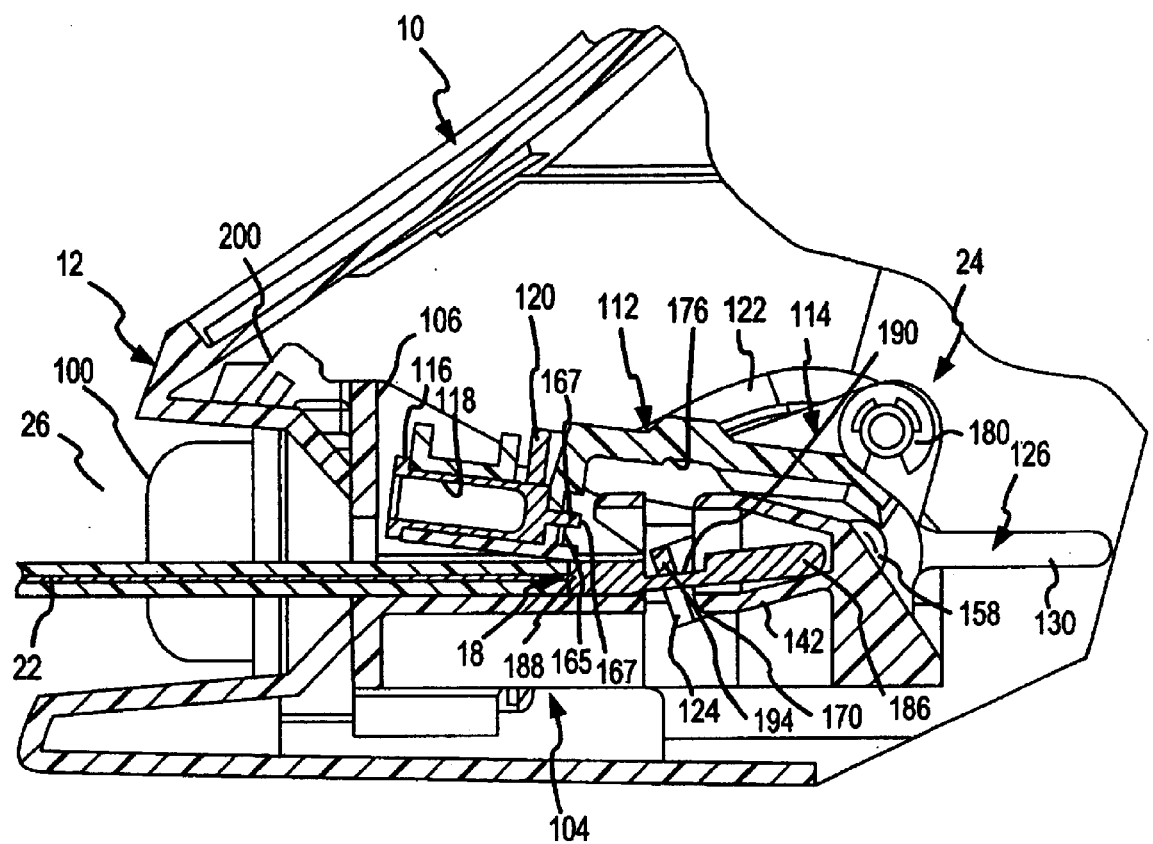
FIG. 6 is a side cross-sectional view of the multi-plug connector device shown in FIG. 4, taken substantially in the plane of line X—X in FIG. 4, and through a passageway in which a rolled sheet metal connector plug of the type shown in FIG. 1 is connected to the multi-plug connector device.
Figure 7:
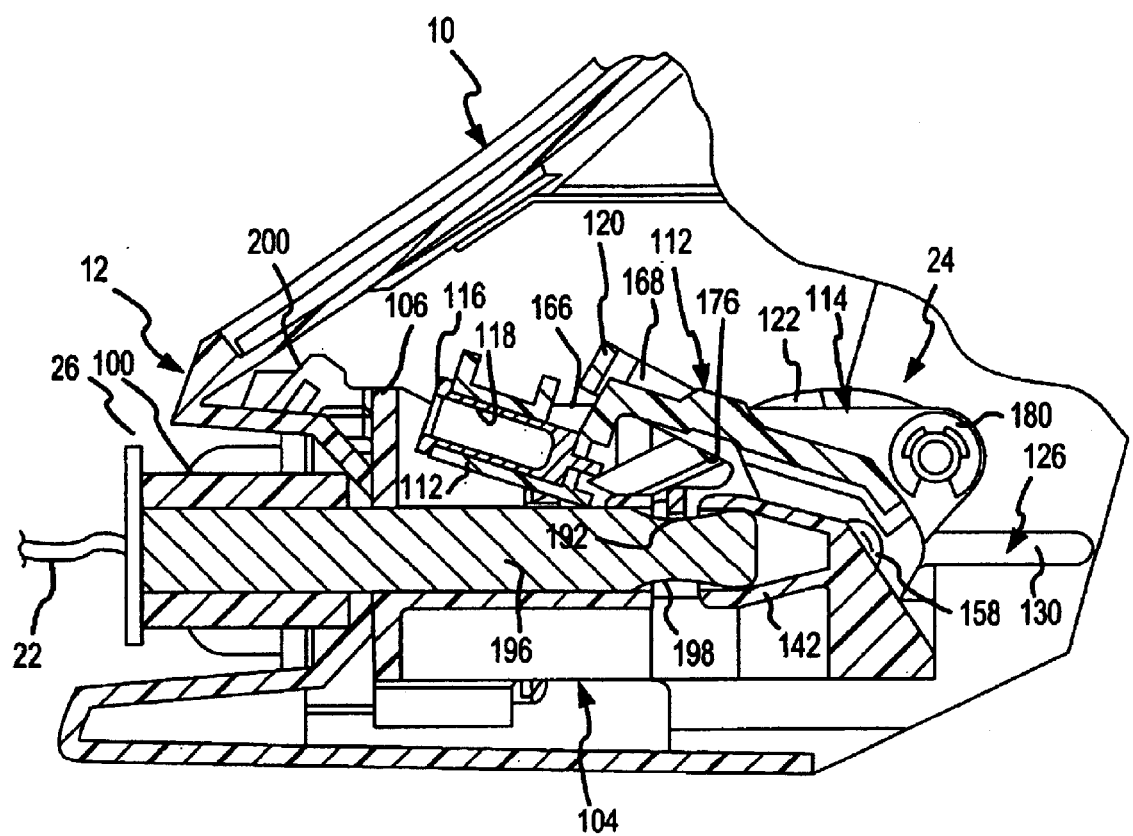
FIG. 7 is a side cross-sectional view of the multi-plug connector device shown in FIG. 4, taken substantially in the plane of line X—X in FIG. 4, and through a passageway in which a Bovie connector plug of the type shown in FIG. 1 is connected to the multi-plug connector device.

The multi-plug connector device 24 includes an actuator button 100 located in the receptacle 26 which must be pressed to accept and release the rolled sheet metal connector plug 18 and the Bovie accessory connector 20. The banana pin connector plug 16 can be inserted into and released from the multi-plug connector device 24 without moving the actuator button 100. All of the connector plugs 16, 18 and 20 are inserted into the multi-plug connector device 24 through an opening 102 located in the receptacle 26 in the front panel 12. The manner in which the multi-plug connector device 24 mechanically and electrically connects to and disconnects from the banana connector plug 16, the rolled sheet metal connector plug 18 and the Bovie connector plug 20 are shown in FIGS. 5–7, respectively.

Figure 2:
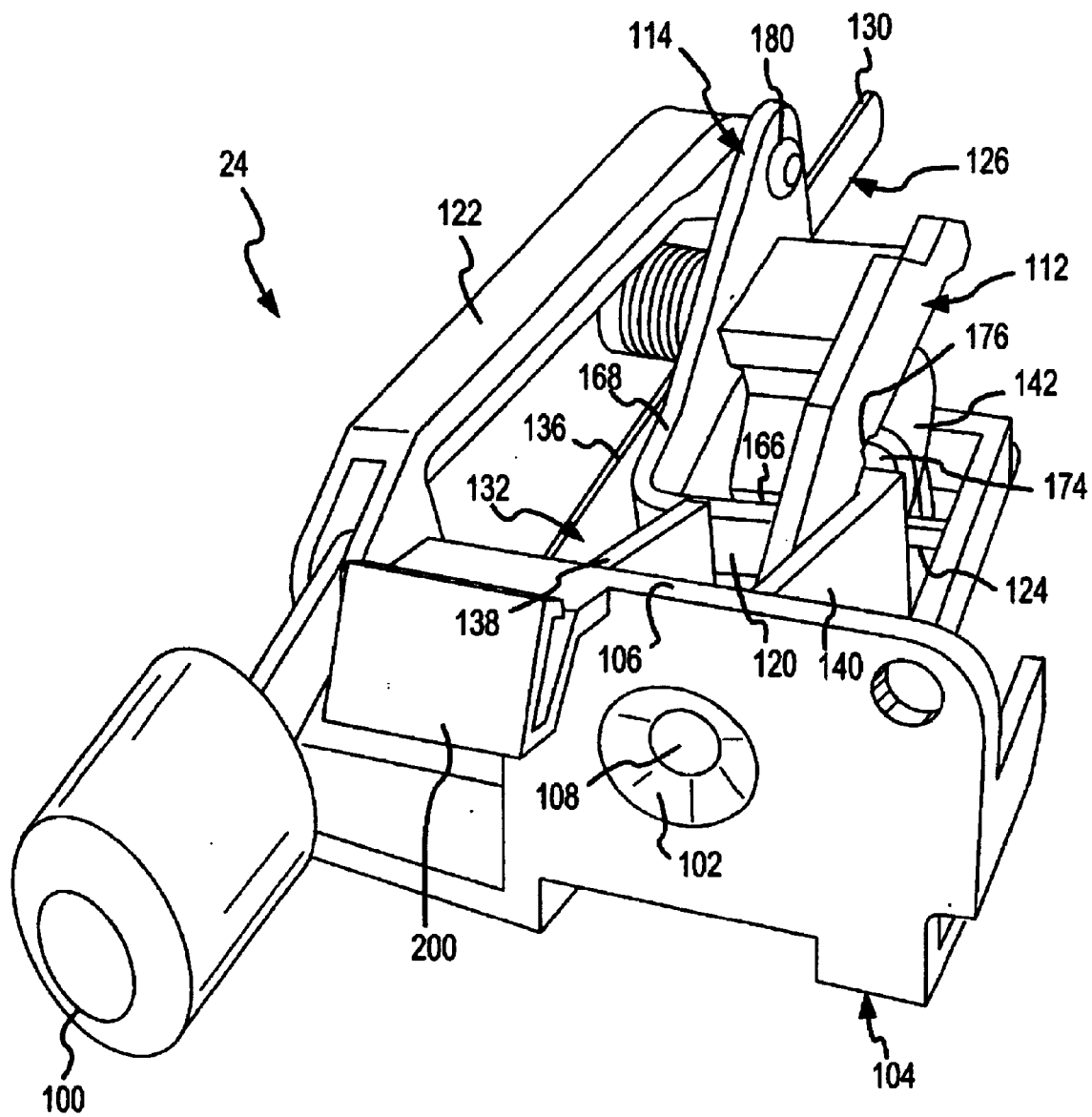
FIG. 2 is a front perspective view of a multi-plug connector device located behind a front panel of the electrosurgical generator shown in FIG. 1, in which the present invention is embodied.
Figure 3:
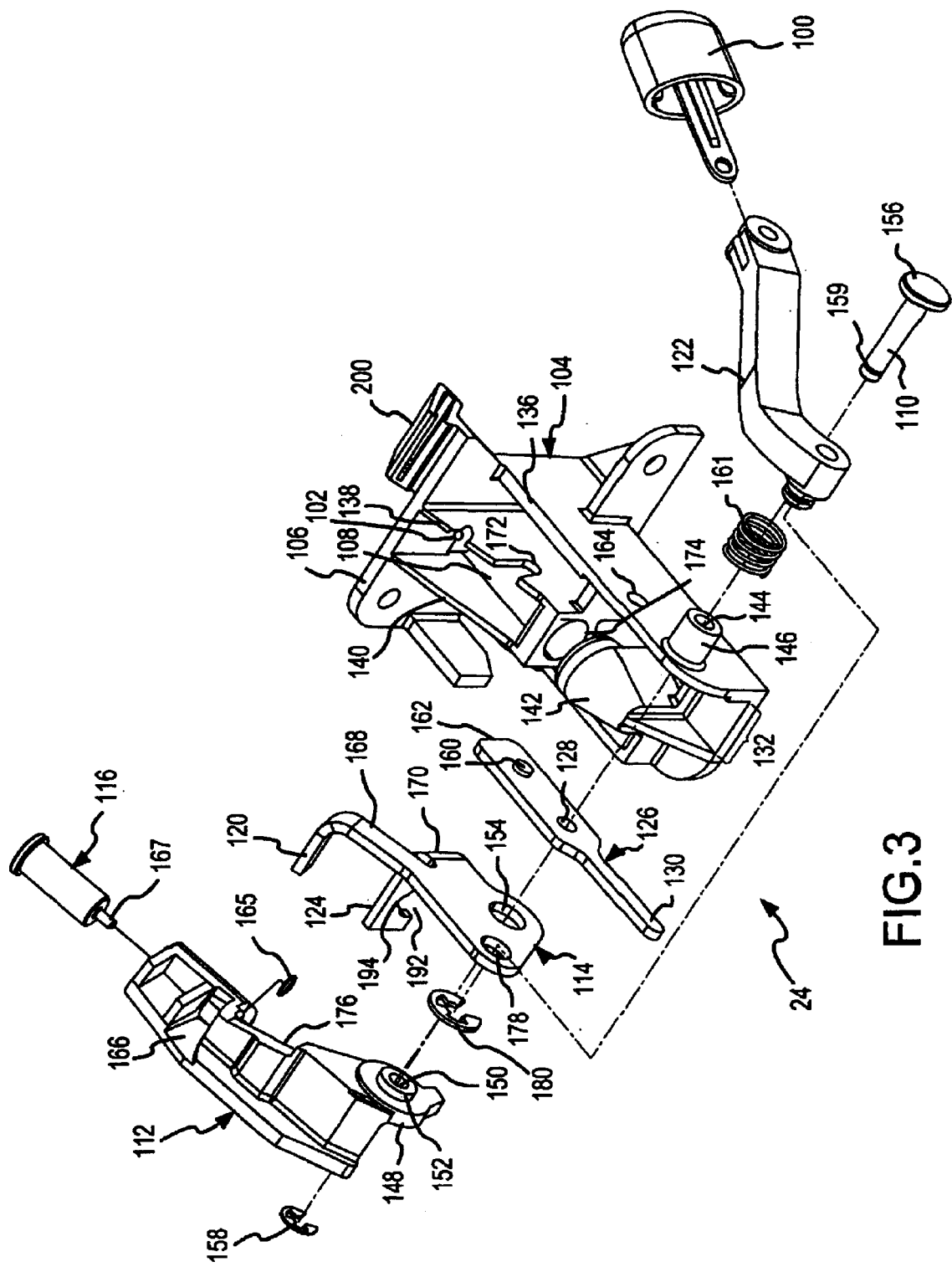
FIG. 3 is an exploded rear perspective view of the multi-plug connector device shown in FIG. 2.
Figure 4:
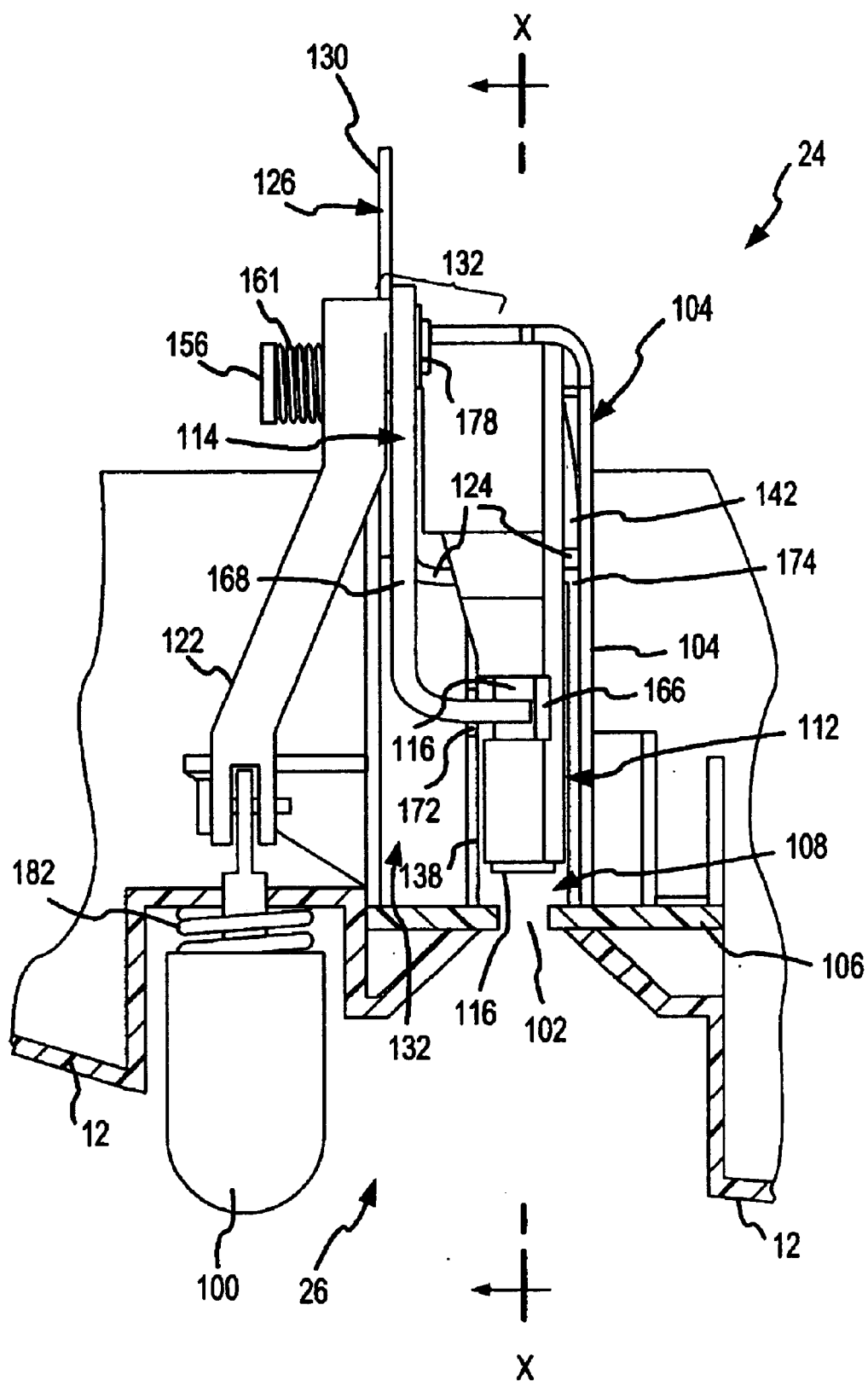
FIG. 4 is a top view of the multi-plug connector device shown in FIGS. 2 and 3, shown in relation to a horizontally sectioned portion of the front panel of the electrosurgical generator shown in FIG. 1.

Details concerning the general structure and function of the multi-plug connector device 24 are shown in FIGS. 2–4. A base 104 constitutes the main structural support member for the multi-plug connector device 24. The base 104 includes a front wall 106 (FIG. 2) which is connected to the back side of the front panel 12 of the electrosurgical generator as shown in FIG. 4. The opening 102 is formed in the front wall 106. Connected to the front panel 12, the base 104 supports the multi-plug connector device 24 behind the front panel 12 in a manner which aligns the opening 102 in the receptacle 26 of the front wall 106, thereby allowing the connector plugs 16, 18 and 20 to be inserted into and removed from the multi-plug connector device 24 through a passageway 108 that extends rearward into the connector device 24 from the opening 102.

A pivot pin 110 is connected to the base 104 and generally extends transversely across the rear of the base 104, as shown in FIG. 3. A pivot arm 112 and a pivot electrode 114 are connected to the pivot pin 110 and pivot about the axis through the pivot pin 110. The pivot pin 110 allows the pivot arm 112 and pivot electrode 114 to pivot into the different configurations shown in FIGS. 5–7, to allow each of the different connector plugs 16, 18 and 20 to be connected. The pivot pin 110 is preferably metallic. The base 104 is preferably made from a molded plastic electrical insulation material.

A socket connector 116 is located at a forward end of the pivot arm 112. The banana connector plug 16 is inserted within a socket 118 of the socket connector 116 (FIG. 5). The pivot arm 112 is normally pivoted downward in the passageway 108 to the position illustrated in FIG. 5, so that the socket 118 of the socket connector 116 is aligned with the opening 102 in the front wall 106 of the base 104. In this manner, the banana connector plug 16 can be inserted into and removed from the socket 118 to connect and disconnect the banana connector plug 116 from the multi-plug connector device 24. Electrical conductivity with the socket connector 116 is established by mechanical contact of a front contact arm 120 of the pivot electrode 114.

Depressing the actuator button 100 transfers force through a link 122 which is connected between the actuator button 100 and the pivot electrode 114. The pivot electrode 114 pivots around the axis through the pivot pin 110 and causes a middle contact arm 124 of the pivot electrode 114 to contact the pivot arm 112 and move the socket connector 116 upward (FIGS. 6 and 7). The socket connector 116 and a forward end of the pivot arm 112 move upward in the passageway 108 out of alignment with the opening 102 and permit the rolled sheet metal connector plug 18 to be inserted into the passageway 108 of the multi-plug connector device 24 (FIG. 6). When the force from the actuator button 100 is released, the pivot arm 112 and the pivot electrode 114 move downward, to the position shown in FIG. 6. In this position, the middle contact arm 124 comes down into mechanical and electrical contact with the rolled sheet metal connector plug 18. The actuator button 100 must be depressed to raise the pivot electrode 114 and the middle contact arm 124 out of contact with the rolled sheet metal connector plug 18, to release the connector plug 18 from the multi-plug connector device 24 and allow it to be withdrawn from the connector device 24.

The actuator button 100 must also be depressed to insert and remove the Bovie connector plug 20. With the pivot arm 112 and the pivot electrode 114 pivoted to an upper position within the passageway 108 with the socket connector 116 and a forward end of the pivot arm 112 out of alignment with the opening 102, the Bovie connector plug 20 is inserted through the opening 102 (FIG. 7). Thereafter, the depression force on the actuator button 100 is released, and the pivot arm 112 and the pivot electrode 114 move downward to the position shown in FIG. 7. The middle contact arm 124 contacts the Bovie connector plug 20 to establish mechanical and electrical contact.

The electrical contact with each of the connector plugs 16, 18, and 20 is therefore through the pivot electrode 114. An electrical contact member 126 contacts the pivot electrode 114 as a result of their side-by-side contact and as a result of the pivot pin 110 extending through a hole 128 formed in the contact member 126. Electrical power is conducted to a rear extension portion 130 of the electrical contact member 126 and through the pivot electrode 114 to the connector plug 16, 18 or 20 connected to the multi-plug connector device 24.

A front-to-back slot 132 extends generally parallel to the front-to-back passageway 108. The slot 132 and the passageway 108 extend rearwardly from the front wall 106 to a rear end of the base 104. The slot 132 is defined between walls 136 and 138 that extend from the front wall 106 to the rear end of the base 104. The passageway 108 is defined between walls 138 and 140. The wall 140 also extends from the front wall 106 to the rear end of the base 104. The connector plugs 16, 18 and 20 are inserted into the passageway 108 through the opening 102 in the front wall 106. A conical receptacle 142 is formed in the base 104 at the rear end of the passageway 108. The conical receptacle 142 receives the forward tip ends of the rolled sheet metal connector plug 18 and the Bovie connector plug 20 (FIGS. 6 and 7).

The pivot arm 112, the pivot electrode 114, and the electrical contact member 126 are retained in the slot 132 and pivot around an axis through the pivot pin 110. The pivot pin 110 extends through a hole 144 in a sleeve 146 which is formed integrally with the wall 136 and which extends outward therefrom. The sleeve 146 provides sufficient support along the axis of the pivot pin 110 to hold the pivot arm 112, pivot electrode 114 and electrical contact member 126 in a relatively fixed position for pivoting around the pivot pin 110. Positioned in this manner, the pivot pin 110 extends transversely across the rear end of the slot 132, as shown in FIG. 3.

The pivot arm 112 includes a connection flange 148 through which a hole 150 is formed to receive the pivot pin 110. A cylindrical shoulder 152 surrounds the hole 150 and forms a shaft which is received within a hole 154 formed in the pivot electrode 114. The axial length of the cylindrical shoulder shaft 152 is approximately equal to the thickness of the pivot electrode 114. In this manner, the pivot electrode 114 contacts the surface of the flange 154 and pivots about the cylindrical shoulder shaft 152. The pivot pin 110 extends through the hole 128 of the electrical contact member 126. The electrical contact member 126 thereby contacts a surface of the pivot electrode 114. This assembled relationship of the pivot arm 112, the pivot electrode 114 and the electrical contact member 126 are maintained by the pivot pin 110. An enlarged head 156 of the pivot pin 110 rests against the sleeve 146 and a keeper washer 158 is attached within an annular groove 159 formed at the other end of the pivot pin 110, to maintain this assembled relationship. A spring 161 biases the head 156 outward relative to the wall 136, to maintain the pivot arm 112, the pivot electrode 114 and the electrical contact member 126 in contact with one another as described.

With the contact member 126 located between the wall 136 and the pivot electrode 114, one flat side of the contact member 126 contacts an adjacent side of the pivot electrode 114 and the other flat side of the contact member 126 contacts the wall 136. The electrical contact member 126 does not pivot around the pivot pin 114, because a protrusion 160 extends from a front extension portion 162 of the contact member 126 into a hole 164 formed in the wall 136. The rear extension portion 130 of the electrical contact member 126 extends beyond the rear edge of the base 104 of the multi-plug connector device 24. The extension 130 makes electrical contact with a spring clip of a circuit board (neither shown) located within the electrosurgical generator 10 (FIG. 1) in a manner which is more completely described in the above-mentioned U.S. patent application for Electrosurgical Generator and Method with Removable Front Panel Having Replaceable Electrical Connection Sockets and Illuminated Receptacles. An electrical path for conducting the electrosurgical power is thus established from the spring clip of a circuit board (neither shown) within the electrosurgical generator, through the rear extension portion 130 of the electrical contact member 126 and to the pivot electrode 114 and its contact arms 120 and 124. The contact arms 120 and 124 are electrically connected to the one of the plug connection 16, 18 or 20 which is inserted into the multi-plug connector device 24.

The flange 148 is offset from the main portion of the pivot arm 112 to position the main portion of the pivot arm 112 above and in the passageway 108. The front end of the pivot arm 112 is aligned with the hole 102 within the passageway 108 to support the socket connector 116 in alignment with the openings 102 and 108 when the pivot arm 112 is in its downward position (FIG. 5). The main portion of the pivot arm 112 is made of electrical insulation material, such as plastic.

The forward end of the pivot arm 112 includes a hole to accept the socket connector 116. A keeper 165 is attached to a knob 167 on the rear of the sleeve to hold the socket connector 116 in place in the pivot arm 112. The socket connector 116 is metallic and electrically conductive and has a generally cylindrical exterior configuration. The socket 118 is also generally cylindrically shaped and is located within the interior of the socket connector 116 to receive the banana connector plug 16 (FIG. 1). The forward end of the pivot arm 112 includes a slot 166 which exposes the socket connector 116 for electrical and mechanical contact by the front contact arm 120 of the pivot electrode 114.

The pivot electrode 114 includes an upper extension portion 168 and a lower extension portion 170. The upper extension portion 168 extends forward from the pivot axis of the pivot electrode 114 to a relatively greater extent than the lower extension portion 170. The front contact arm 120 extends transversely from the forward end of the upper extension portion 168, and the middle contact arm 124 extends transversely from the forward end of the lower extension portion 170. The front contact arm 120 extends into the slot 166 located at the forward end of the pivot arm 112 to make electrical contact with the socket connector 116. A notch 172 is formed in the wall 138 to permit the front contact arm 120 of the pivot electrode 114 to extend into the slot 166 and contact the socket connector 116. The middle contact arm 124 extends transversely from the forward end of the lower extension portion 170 into a space 174 which is located near the rear end of the passageway 108 and in front of the conical receptacle 142 and between the walls 138 and 140.

A downward facing recess 176 is formed in the pivot arm 112 at a middle location between the forward end of the pivot arm 112 where the socket connector 116 is located and a rear end of the pivot arm 112 near the hole 150. The middle contact arm 124 of the pivot electrode 114 extends through the space 174 and into the recess 176. Positioned within the recess 176, the middle contact arm 124 contacts the pivot arm 112 to pivot the pivot arm 112 and lift the front end of the pivot arm 112 upward when the middle contact arm 124 of the pivot electrode 114 moves upward as a result of the pivoting movement of the pivot electrode 114.

The two contact arms 120 and 124 effectively control the pivoting movement of the pivot arm 112, allowing the pivoting movement of the pivot electrode 114 to control the pivoting movement of the pivot arm 112. Because of the geometric relationship of the contact arms 120 and 124 within the slot 166 and the recess 176, respectively, there is a limited amount of free pivot movement of the pivot arm 112 between the points where the contact arms 120 and 124 contact the pivot arm 112. The front contact arm 120 is thus in the position to contact the socket connector 116 mechanically and electrically and force the forward end of the pivot arm 112 down when the front contact arm 120 moves downward. In this manner, the front contact arm 120 holds the socket connector 116 down and in alignment with the opening 102 (FIG. 5). The middle contact arm 124 contacts the recess 176 of the pivot arm 112 to lift the pivot arm 112 whenever the pivot electrode 114 is pivoted.

The pivot electrode 114 is pivoted by motion transferred from the link 122. The rear end of the link 122 is connected to a hole 178 in the pivot electrode 114, and is retained in position in the hole 178 by a keeper washer 180. The front end of the link 122 is connected to the actuator button 100, which is located within the receptacle 26 in the front panel 12 (FIGS. 1 and 4). A spring 182 biases the button 100 forward relative to the front panel, as shown in FIG. 4, thereby normally applying forward force to the link 122. Thus, the pivot electrode 114 and the arm 112 are normally biased in the passageway 108 to position the socket connector 116 with the socket 118 directly aligned with the opening 102 when the actuator button 100 is not depressed.

Depressing the button 100 compresses the spring 182 and forces the link 122 rearwardly toward the rear of the base 104. The rearward movement of the link 122 causes the pivot electrode 114 to pivot in a direction which causes the middle contact arm 124 to move upward. The middle contact arm 124 moves up into the recess 176 and pivots the pivot arm 112 which causes the forward end of the pivot arm 112 to move upward. When the actuator button 100 is not depressed, the pivot electrode 114 and the pivot arm 112 move downward by gravity and under the influence of bias force from the spring 182 transferred through the link 122, to locate the middle contact arm 124 at a downward position within the space 174 and to position the front contact arm 120 within the notch 172 in the wall 138, as is generally understood from FIGS. 3 and 5.

As shown in FIG. 5, the banana pin accessory connector plug 16 has a prong 184 that is inserted through the opening 102 and into the passageway 108 and into the socket 118 of the socket connector 116, when socket 118 and pivot arm 112 are resting in the downward pivoted position within the passageway 108. Likewise, the front contact arm 120 of the upper extension portion 168 of the pivot electrode 114 is resting in the downward position within the notch 172 and slot 166 (FIG. 3) in contact with the socket connector 116. The actuator button 100 and the link 122 are both in their forward position which exists when actuator button 100 is not depressed (FIG. 4).

The biasing force of the spring 182 holds the pivot electrode 114 in the pivoted position with the front contact arm 120 of the upper extension portion 168 of the pivot electrode 114 contacting the socket connector 116 and forcing the pivot arm 112 downward with the socket 118 in alignment with the opening 102. The prong 184 of the connection plug 16 is directly inserted into the socket 118 of the socket connector 116. The prong 184 is held in the socket 118 by frictional resistance. The electrosurgical power is conducted through the rearward extension 130 of the electrical contact member 126, through the pivot electrode 114 to the front contact arm 120, and from the front contact arm 120 through the socket connector 116 and into the prong 182. The electrosurgical power flows through the conductor 22 to the foot-switched monopolar handpiece 14 and from the electrode 68 (FIG. 1) to the patient. The connection plug 16 is removed by pulling the prong 182 from the socket 118 without depressing the actuator button 100.

The connection of the rolled sheet metal accessory connector plug 18 to the multi-plug connector device 24 is shown in FIG. 6. The connector plug 18 includes a front generally tubular section 186 and a rear section 188 which is connected to the conductor 22. A generally rectangular slot 190 exists in the connector plug 18 between the front section 186 and the rear section 188. The slot 190 extends transversely across the connector plug 18 to separate the front section 186 from the rear section 186.

The actuator button 100 must be depressed to pivot the pivot electrode 114 so that the socket connector 116 and the front end of the pivot arm 112 are elevated within the passageway 108, out of alignment with the opening 102. The rolled sheet metal connector plug 18 is then inserted through the opening 102 and into the passageway 108 by pushing on the conductor 22 until the front section 186 of the connector plug 18 is inserted completely within the conical receptacle 142 of the base 104. The force on the actuator button 100 is then released, and the spring 182 moves the pivot electrode 114 so that the middle contact arm 124 of the lower extension portion 170 moves downward. The middle contact arm 124 includes large and small semicircular cutouts 192 and 194 (FIG. 3). The small cutout 194 is within and at the top of the large cutout 192. The small cutout 194 of the middle contact arm 124 extends into the rectangular slot 190 of the connector plug 18 and rests on top of, and makes a mechanical and electrical connection with the connection plug 18 at the rectangular slot 190. The electrosurgical power from the internal components of the electrosurgical generator is conducted through the rear extension 130 of the electrical contact member 126 to the pivot electrode 114, and from the middle contact arm 124 to the rolled sheet metal connector plug 18. From the connector plug 18, the electrosurgical power travels through the conductor 22 to the foot-switched monopolar handpiece 14 and from its electrode 68 (FIG. 1) into the tissue of the patient.

The actuator button 100 and the link 122 both remain slightly rearward of their forwardmost position when the rolled sheet metal connector plug 18 is contacted in the manner described, because the middle contact arm 124 is not allowed to move downward within the space 174 to its lowermost position (cf. FIG. 5). Under the bias force from the spring 182, the middle contact arm 124 of the pivot electrode 114 is forced into the rectangular slot 190 of the connector plug 18. This force prevents the connector plug 18 from being accidentally pulled from this connected relationship within the multi-plug connector device 24. The front section 186 of the connector plug 18 is held in the conical receptacle 142 by the retaining force of the middle contact arm 124 in the rectangular slot 190. To remove the connector plug 18 from the multi-plug connector device 24, the actuator button 100 must be depressed to pivot the middle contact arm 124 up and out of the slot 190 so the connection plug 18 can then be pulled from the multi-plug connector device 24. The actuator button 100 is then released.

As shown in FIG. 7, the Bovie #12 accessory connector plug 20 includes a front solid metallic prong 196 which is electrically connected to the conductor 22. The prong 196 includes a reduced-circumference necked area 198 near the tip end of the prong 196. To insert the Bovie connector plug 20 into the multi-plug connector device 24, the forward end of the pivot arm 112 and the middle contact arm 124 of the lower extension portion 170 of the pivot electrode 114 are moved upward in the passageway 108 out of alignment with the conical receptacle 142. To do so, the actuator button 100 is depressed. The prong 196 is then inserted through the opening 102 and passageway 108 until the tip end of the prong 196 is located within the conical receptacle 142. The force on the actuator button 100 is then released to allow the pivot electrode 114 to move the middle contact arm 124 downward.

The downward movement of the middle contact arm 124 positions the large cutout 192 (FIG. 3) on the top of the necked area 198 of the prong 196, thereby establishing a mechanical and electrical contact of the middle contact arm 124 with the prong 196 of the Bovie connector plug 20. Because of the contact of the middle contact arm 124 with the necked area 198, the pivot electrode 114 can not pivot the middle contact arm 124 to its lowermost position (cf. FIG. 5). The spring 182 remains slightly compressed and transfers force from the actuator button 100 and the link 122 to the pivot electrode 114 to maintain the middle contact arm 124 in contact with the necked area 198. The prong 196 is held in the multi-plug connector device 24 by resistance from the middle contact arm 124 in the necked area 198. Electrosurgical power is conducted from the rear extension 130 of the contact member 126 to the pivot electrode 114 and the middle contact arm 124, and into the prong 196 of the Bovie connector plug 20. The electrosurgical power flows from the prong 196 through the conductor 22 to the active electrode 68 of the foot-switched monopolar handpiece 14 (FIG. 1).

To remove the connection plug 20 from the multi-plug connector device 24, the actuator button 100 is depressed to pivot the middle contact arm 124 up out of the necked area 198. The Bovie connector plug 20 is then be pulled from the multi-plug connector device 24. The actuator button 100 is then released.

A further improvement from the multi-plug connector device 24 is that the base 104 includes a light emitter support element 200 (FIGS. 2 and 3) that supports an optical light emitter (not shown) to illuminate the receptacle 26 in the front panel 12 (FIGS. 1 and 4). Illuminating the receptacle 26 makes it easier for the user to insert the connector plugs 16, 18 or 20 into the receptacle 26 (FIG. 1), to remove the connector plugs 16, 18 or 20 from the opening 102, and to push the actuator button 100 when necessary in conjunction with the insertion and removal of the connector plugs 16, 18 and 20. Illuminating the receptacle 26 in this manner is a significant improvement in electrosurgical generators which are typically used in darkened environments. More details concerning the optical light emitter and the illumination of the receptacle are described in the above identified U.S. patent application for Electrosurgical Generator and Method with Removable Front Panel Having Replaceable Electrical Connection Sockets and Illuminated Receptacles.

The multi-plug connector device 24 has the advantage of being able to establish an electrical connection to a plurality of conventional connector plugs currently used to connect foot-switched monopolar handpieces and instruments to an electrosurgical generator 10 (FIG. 1). Thus any of the foot-switched monopolar handpieces which uses any one of the banana pin accessory connector plug 16, the rolled sheet metal accessory connector plug 18 or the Bovie accessory connector plug 20 can be directly accepted by the multi-plug connector device 24, without the use of an adapter. The necessity to obtain, account for and use adapters is avoided altogether as a result of the present invention.

Presently preferred embodiments of the invention and its improvements have been described with a degree of particularity. This description has been made by way of preferred example. The scope of the invention is defined by the following claims, which should not be unnecessarily limited by the detailed description of the preferred embodiments set forth above.

What is claimed is:

1. A multi-plug connector device for mechanically and electrically connecting multiple different types of connector plugs of foot-switched monopolar electrosurgical handpieces to an electrosurgical generator, comprising:

a base defining a passageway through which the connection plugs are inserted for connection to the connector device and withdrawn for disconnection from the connector device;

a pivot arm having a forward end and a socket connector located at the forward end, the pivot arm connected relative to the base to pivot between a first position in which the socket connector is located in alignment with the passageway and a second position in which the socket connector is located out of alignment with the passageway, the socket connector including a socket for receiving a first type of connector plug inserted through the passageway into the socket when the pivot arm is in the first position;

a pivot electrode having a forward contact arm and a middle contact arm, the pivot electrode connected relative to the base to pivot between a first position and a second position, the first position of the pivot electrode contacting the forward contact arm with the socket connector when the pivot arm is in the first position, the second position of the pivot electrode locating the middle contact arm within the passageway in contact with a second type of connector plug inserted through the passageway when the pivot arm is in the second position; and an electrical contact member electrically connected to the pivot electrode to conduct current to the pivot electrode.

2. A multi-plug connector device as defined in claim 1, wherein:

the pivot electrode is connected the pivot arm to pivot the pivot arm into the second position when the pivot electrode is pivoted to the second position.

3. A multi-plug connector device as defined in claim 1, wherein:

the forward contact arm and the middle contact arm are interconnected to move the pivot arm into the second position upon pivoting the pivot electrode to the second position and to move the pivot arm into the first position upon pivoting the pivot electrode to the first position.

4. A multi-plug connector device as defined in claim 3, wherein:

the base further defines a space extending transversely across the passageway; and the middle contact arm moves within the space and through the passageway upon movement of the pivot arm from the second position to the first position.

5. A multi-plug connector device as defined in claim 4, wherein:
the pivot arm positions the socket connector at a location in front of the space extending transversely across the passageway when the pivot arm is in the first position.

6. A multi-plug connector device as defined in claim 5, wherein:
the base further defines an opening at one end of the passageway through which the connector plugs are inserted into and withdrawn from the passageway; and
the base further defines a receptacle located at the opposite end of the passageway from the opening, the receptacle receiving an end of the second type of connector when the middle contact arm contacts the second type of connector.

7. A multi-plug connector device as defined in claim 1, wherein:
the base further defines an opening at one end of the passageway through which the connector plugs are inserted into and withdrawn from the passageway;
the base further defines a receptacle located at the opposite end of the passageway from the opening, the receptacle receiving an end of the second type of connector when the middle contact arm contacts the second type of connector;
the pivot arm positions the socket connector at a location in front of the receptacle within the passageway and positions the socket in alignment with the opening when the pivot arm is in the first position;
the second type of connector plug includes a tip end which is received within the receptacle; and
the pivot electrode moves the middle contact arm into the passageway in front of the receptacle and in contact with the second type of connector plug when the tip end of the second type of connector plug is within the receptacle when the pivot electrode is in the second position.

8. A multi-plug connector device as defined in claim 1, wherein:
the forward contact arm and a middle contact arm are positioned to contact the pivot arm and to move the pivot arm from the first position into the second position upon pivoting the pivot electrode from the first position to the second position and to move the pivot arm from the second position into the first position upon pivoting the pivot electrode from the second position to the first position.

9. A multi-plug connector device as defined in claim 8, further comprising:
an actuator connected for movement relative to the base to pivot the pivot electrode between the first and second positions.

10. A multi-plug connector device as defined in claim 8, wherein:
the connector device is located within an electrosurgical generator behind a housing panel of the electrosurgical generator.

11. A multi-plug connector device as defined in claim 10, wherein:
the housing panel includes an opening through which a portion of each connector plug is extended when connected to the connector device; and
the passageway is positioned in alignment with the opening in the housing panel.

12. A multi-plug connector device as defined in claim 11, wherein:
an actuator exposed at the housing panel and connected for movement relative to the housing panel and the connector device and connected to the pivot electrode to pivot the pivot electrode between the first and second positions.

13. A multi-plug connector device as defined in claim 12, wherein:
the first type of connector plug is a banana pin connector plug; and
the second type of connector plug is one of a rolled sheet metal connector plug or a Bovie connector plug.

14. In an electrosurgical generator, a single multi-plug connector device defining a passageway through which each of a banana pin connector plug, a rolled sheet metal connector plug and a Bovie connector plug is inserted and through which each inserted connector plug is withdrawn, each connector plug electrically connected to a foot-switched electrosurgical handpiece, the multi-plug connector device including at least one contact element operatively positioned within the passageway to mechanically and electrically connect to and to retain each one connected banana pin connector plug, rolled sheet metal connector plug and Bovie connector plug inserted within the passageway.

15. A multi-plug connector device for mechanically and electrically connecting each one of a banana pin connector plug, a rolled sheet metal connector plug and a Bovie connector plug to an electrosurgical generator, comprising:
a base defining a passageway through which the connection plugs are inserted for connection to the connector device and withdrawn for disconnection from the connector device;
a socket connector defining a socket into which the banana pin connector plug is inserted;
a first member connected to the socket connector and operative to move the socket connector and the socket into and out of alignment with the passageway;
a contact arm for contacting the rolled sheet metal connector plug and the Bovie connector plug;
a second member connected to the contact arm and operative to move the contact arm into and out of alignment with the passageway; and
an interconnection between the first and second members which moves the socket connector into alignment with the passageway and the contact arm out of alignment with the passageway in one operative position and which moves the socket connector out of alignment with the passageway and the contact arm into alignment with the passageway in another operative position.

16. A multi-plug connector device as defined in claim 15, further comprising:
an electrode member electrically connecting the socket connector and the contact arm.

17. A multi-plug connector device as defined in claim 15, further comprising:
an actuator connected to impart the movement to one of the first or second members to cause the interconnection to move the other one of the first or second members.

18. A multi-plug connector device as defined in claim 15, wherein the rolled sheet metal connector plug includes a front section and a rear section separated by a slot, and the Bovie connector plug includes a prong with a necked area surrounding a forward tip of the prong, and wherein:

the contact arm extends into the slot between the front section and the rear section when contacting the rolled sheet metal connector plug; and the contact arm extends into the necked area of the forward tip of the prong when contacting the lowly connector plug.

19. A multi-plug connector device as defined in claim 18, wherein:

the contact arm must be removed from the slot of the rolled sheet metal connector plug and from the necked area of the Bovie connector plug to remove the rolled sheet metal connector plug and the Bovie connector plug from the multi-plug connector device.

20. A method of electrically and mechanically connecting each one of a banana pin connector plug, a rolled sheet metal connector plug and a Bovie connector plug to an electrosurgical generator one connector plug at a time, comprising:

defining a passageway through which each of the connection plugs are inserted for connection to and withdrawn for disconnection from the electrosurgical generator;

moving a socket into the passageway into which the banana pin connector plug may be inserted; and moving a contact arm into the passageway by which to contact the rolled sheet metal connector plug and the Bovie connector plug.

21. A method as defined in claim 20, further comprising:

moving the contact arm out of the passageway when the socket is moved into the passageway; and moving the socket out of the passageway when the contact arm is moved into the passageway.

22. A method as defined in claim 21, further comprising:

interrelating the movement of the socket and the contact arm into and out of the passageway to locate only one of the socket or the contact arm in the passageway at one time.

23. A method as defined in claim 22, further comprising:

extending the passageway from an exterior housing of the electrosurgical generator into an interior of the electrosurgical generator within the housing; and manually initiating the movement of the socket and the contact arm exteriorly of the exterior housing of the electrosurgical generator.

24. A method as defined in claim 20, further comprising:

positioning a receptacle at a terminal end of the passageway; and locating a tip end of each of the rolled sheet metal connector plug and the Bovie connector plug within the receptacle upon moving the contact arm into contact with the rolled sheet metal connector plug and the Bovie connector plug.

25. A method as defined in claim 24, further comprising:

moving the contact arm transversely into contact with the rolled sheet metal connector plug and the Bovie connector plug.

26. A method as defined in claim 24, further comprising:

moving the contact arm into and out of the passageway at a position in front of the receptacle relative to the direction of insertion of the connector plugs in the passageway.

27. A method as defined in claim 24, further comprising:

moving the socket into and out of the passageway at a position in front of the receptacle relative to the direction of insertion of the connector plugs in the passageway.

28. A method as defined in claim 24, further comprising:

moving the contact arm into and out of the passageway at a position in front of the receptacle relative to the direction of insertion of the connector plugs in the passageway; and moving the socket into and out of the passageway at a position in front of the receptacle and the position at which the contact arm moves into and out of the passageway relative to the direction of insertion of the connector plugs in the passageway.

29. A method as defined in claim 20, wherein the rolled sheet metal connector plug includes a front section and a rear section separated by a slot, and the Bovie connector plug includes a prong with a necked area surrounding a forward tip of the prong, and further comprising:

moving the contact arm into the slot to contact the rolled sheet metal connector plug; and moving the contact arm into the necked area to contact the Bovie connector plug.

30. A method as defined in claim 29, further comprising:

retaining the rolled sheet metal connector plug by locating the contact arm in the slot; and retaining the Bovie connector plug by locating the contact arm in the neck area.

31. An invention as defined in claim 14, wherein:

the contact element includes a portion which is moves into and out of the passageway according to the type of connector plug which is inserted within the passageway.

32. An invention as defined in claim 14, wherein:

the contact element includes different portions which mechanically and electrically connect to and retain different ones of the connector plugs.

33. An invention as defined in claim 32, further comprising:

an interconnection between the portions of the contact element which moves the one portion into alignment with the passageway and moves the other portion out of alignment with the passageway when mechanically and electrically connecting to and retaining one of the connector plugs and which moves the one portion out of alignment with the passageway and moves the other portion into alignment with the passageway when mechanically and electrically connecting to and retaining another different one of the connector plugs.

34. An invention as defined in claim 33, wherein:

one portion of the contact element comprises a socket.

35. An invention as defined in claim 34, wherein:

another portion of the contact element comprises a contact arm.

36. An invention as defined in claim 33, wherein:

one portion of the contact element comprises a contact arm.

37. An invention as defined in claim 14, wherein:

the contact element includes a socket into which the banana pin connector plug is inserted upon insertion of the banana pin connector plug into the passageway; and the socket is operatively connected to move into and out of the passageway.

38. An invention as defined in claim 14, wherein:

the contact element includes a contact arm for contacting one of the rolled sheet metal connector plug or the Bovie connector plug upon insertion of the rolled sheet metal connector plug or the Bovie connector plug into the passageway, respectively; and the contact arm is operatively connected to move into and out of the passageway.

39. An invention as defined in claim 38, wherein:

the contact element also includes a socket into which the banana pin connector plug is inserted upon insertion of the banana pin connector plug into the passageway; and the socket connector is operatively connected to move into and out of the passageway.

40. An invention as defined in claim 39, further comprising:

an interconnection between the contact arm and the socket which moves the socket into alignment with the passageway and the contact arm out of alignment with the passageway in one operative position and which moves the socket out of alignment with the passageway and the contact arm into alignment with the passageway in another operative position.

* * * * *